United States Patent
Hammerberg

(10) Patent No.: US 7,148,023 B2
(45) Date of Patent: Dec. 12, 2006

(54) IMMUNOGLOBULIN E DETECTION IN MAMMALIAN SPECIES

(75) Inventor: Bruce Hammerberg, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 32 days.

(21) Appl. No.: 10/758,165

(22) Filed: Jan. 15, 2004

(65) Prior Publication Data

US 2005/0196816 A1  Sep. 8, 2005

Related U.S. Application Data

(60) Provisional application No. 60/440,472, filed on Jan. 16, 2003.

(51) Int. Cl.
*G01N 33/53* (2006.01)
*G01N 33/577* (2006.01)
*C07K 16/00* (2006.01)
*C07K 16/42* (2006.01)

(52) U.S. Cl. ............ 435/7.1; 435/7.93; 435/7.94; 436/548; 530/387.1; 530/387.9; 530/388.1; 530/391.3

(58) Field of Classification Search ........... 530/387.1, 530/388.1, 391.3, 387.9; 435/810
See application file for complete search history.

(56) References Cited

U.S. PATENT DOCUMENTS

| | | |
|---|---|---|
| 5,091,313 A | 2/1992 | Chang et al. |
| 5,254,671 A | 10/1993 | Chang |
| 5,260,416 A | 11/1993 | Chang |
| 5,342,924 A | 8/1994 | Chang |
| 5,428,133 A | 6/1995 | Chang |
| 5,514,776 A | 5/1996 | Chang |
| 5,614,611 A | 3/1997 | Chang |
| 6,043,345 A | 3/2000 | Saxon et al. |

OTHER PUBLICATIONS

Kuby et al, Immunology, Second edition, pp. 86-96, 1994.*

Cretien et al.; "A Monoclonal Anti-IgE Antibody Against An Epitope (Amino Acids 367-376) in the CH3 Domain Inhibits IgE Binding to the Low Affinity IgE Receptor (CD23)" *The Journal of Immunology* 141:9 3128-3134 (1988).

Griot-Wenk et al.; "Characterization of two dog IgE-specific antibodies elicited by different recombinant fragments of the epsilon chain in hens" *Vertinary Immunology and Immunopathology* 64 15-32 (1998).

International Search Report for International Application PCT/US04/03566; Date of mailing Apr. 20, 2005.

Orton et al., Canine IgE Monoclonal Antibody Specific for a Filarial Antigen; Production by a Canine X Murine Heterohybridoma Using B Cells from a Clinically Affected Lymph Node, *Immunology*, 85:3, 429-34, Jul. 1995.

William H. Wong, PH.D., Allergen Specific IgE, *Technical Bulletin*, *Diagnostic Laboratory Services, Inc.*, Dec. 3, 1996.

Vernersson et al., Cloning, Structural Analysis, and Expression of the Pig IgE ε Chain, *Immunogenetics*, 46:461-468 (1997).

Hammerberg et al., Auto IgG anti-IgE and IgG X IgE Immune Complex Presence and Effects on ELISA-Based Quantitation of IgE in Canine Atopic Dermatitis, Demodectic Acanasis and Helminthiasis, *Veterinary Immunology and Immunopathology*, 60:33-46 (1997).

Welcome to UniCAP® InvitroSight™ version 3.1, an Interactive Allergy Testing Information and Know-How Service from Pharmacia Diagnostics., *Pharmacia Diagnostics AB*, 2002.

Kalina et al., IgE ELISA Using Antisera Derived from Epsilon Chain Antigenic Peptides Detects Allergen-Specific IgE in Allergic Horses, *Veterinary Immonology and Immunopatholoy*, 92:137-147 (2003).

Dog Purified Immunoglobulin, *Bethyl Laboratories*, Jan. 12, 2004.

* cited by examiner

*Primary Examiner*—Christina Chan
*Assistant Examiner*—Phuong Huynh
(74) *Attorney, Agent, or Firm*—Myers Bigel Sibley & Sajovec, P.A.

(57) ABSTRACT

The present invention provides antibodies (e.g., monoclonal antibodies) that specifically binds to mammalian IgE (e.g., dog IgE). In some embodiments the antibodies bind to an epitope between amino acids 145–166 of mammalian IgE; in other embodiments the antibodies bind to an epitope between amino acids 356–374 of mammalian IgE. The antibodies may be used for allergen reactivity testing in human subjects or animal subjects for veterinary purposes.

12 Claims, No Drawings

IMMUNOGLOBULIN E DETECTION IN MAMMALIAN SPECIES

RELATED APPLICATIONS

This application claims the benefit of U.S. provisional patent application Ser. No. 60/440,472, filed Jan. 16, 2003, the disclosure of which is incorporated by reference herein in its entirety.

FIELD OF THE INVENTION

The present invention concerns methods of detecting IgE antibodies in a subject, and antibody reagents useful therefore.

BACKGROUND OF THE INVENTION

Immunoglobulin E (IgE) is the antibody subclass responsible for, among other things, allergic diseases and anaphylactic shock reactions. Measurement of IgE levels in the blood, tissues and body fluids of mammals is generally required for the accurate diagnosis of allergic diseases. Currently, the detection of IgE in domesticated animals depends on maintaining the native structure of IgE, which unfortunately results in the inaccurate measurement of IgE due to competition by autoantibodies and other serum proteins for IgE binding sites. Heat denaturation of IgE releases these competing molecules and can improve the accuracy of detecting IgE by monoclonal antibodies against heat stable sites. However, highly reliable means and methods for detecting IgE levels are presently lacking.

SUMMARY OF THE INVENTION

The present invention provides antibodies that specifically binds to mammalian IgE. In some embodiments the antibodies bind to an epitope between amino acids 145–166 of mammalian IgE; in other embodiments the antibodies bind to an epitope between amino acids 356–374 of mammalian IgE.

In some embodiments the mammalian IgE to which the antibodies bind is dog IgG.

In some embodiments the antibodies are monoclonal antibodies, e.g. mouse monoclonal antibodies.

In some embodiments the antibodies are coupled to a detectable group; in some embodiments the antibodies are coupled to a solid support; in some embodiments the antibodies are coupled to a member of a specific binding pair (such as biotin and avidin).

The present invention further provides methods of testing for allergen reactivity of an IgE sample. The methods generally comprise the steps of:

(a) contacting a sample containing IgE to a solid support, the solid support having an allergen coupled thereto; and then (b) contacting the solid support to at least one antibody as described above, and then (c) determining the presence or absence of antibody coupled to the solid support, the presence of antibody coupled to the solid support indicating that the IgE in the sample is reactive to the allergen. Where the sample is drawn from a subject, particularly a human or animal subject, the presence of such allergen reactivity is indicative of an allergy to that immunogen in the subject, and/or is an aid to diagnosis of an allergy to that allergen in the subject.

The present invention is described in greater detail in the specification set forth below.

DETAILED DESCRIPTION OF THE PREFERRED EMBODIMENTS

"Allergen" as used herein may be any antigenic or immunogenic material in any form (pure, partially purified, crude) that is used or may be used in allergy testing or as an aid to allergy testing, including but not limited to insect (dust mites particularly house dust mites), pollen, mold, and food allergens (e.g., milk, egg, soy, peanut, and corn allergen).

"Antibody" as used herein refers to all types of immunoglobulins, including IgG, IgM, IgA, IgD, and IgE. The antibodies may be of any species of origin, including (for example) mouse, rat, rabbit, horse, or human, and are preferably mammalian. The term "antibodies" includes antibody fragments and chimeras that retain the ability to bind to the epitope bound by the corresponding intact or complete antibody. Antibodies may be monoclonal or polyclonal.

"Biological sample" as used herein may be any body tissue, fluid, secretion, or excretion that contains IgE immunoglobulins, particularly blood and blood fractions that contain IgE.

"Detectable group" as used herein may be any suitable detectable group, including but not limited to radiolabels (e.g., $^{35}S$, $^{125}I$, $^{131}I$), enzyme labels (e.g., horseradish peroxidase, alkaline phosphatase), fluorescent labels (e.g., fluorescein), and groups (such as biotin) that do not themselves generate a detectable signal, but can be detected by specific binding of another reagent that generates a detectable signal (such as conjugate of avidin with a detectable group).

"Solid support" as used herein may be any suitable solid support, including but not limited to beads, plates, slides or wells formed from materials such as latex or polystyrene.

"Subject" as used herein may be any suitable subject, preferably mammalian, including but not limited to dog, cat, pig, sheep, mouse, rat, horse, human, chimpanzee, and orangutan.

Applicants specifically intend that the disclosures of all U.S. Patent references cited herein be incorporated herein by reference in their entirety.

1. Antibody Production.

Monoclonal antibodies used to carry out the present invention may be produced in a hybridoma cell line according to the technique of Kohler and Milstein, Nature 265, 495–97 (1975). For example, a solution containing the appropriate antigen (such as cat or dog IgE, or a fragment thereof containing the epitope of interest) may be injected into a (preferably mammalian) subject such a goat, rabbit, rat, mouse, etc. Depending on the host species, various adjuvants may be used to increase the immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Booster injections of the antigen may be administered if desired. After a sufficient time, the subject is sacraficed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity (See, e.g., G. Kohler et al., Nature 256: 495–497 (1975); D. Kozbor et al., J.

*Immunol. Methods* 81: 31–42 (1985); R. Cote et al., *Proc. Natl. Acad. Sci.* 80: 2026–2030 (1983); S. Cole et al., *Mol. Cell Biol.* 62: 109–120 (1984)).

In addition, Monoclonal Fab fragments may be produced in *Escherichia coli* by recombinant techniques known to those skilled in the art. See, e.g., W. Huse, *Science* 246, 1275–81 (1989). The antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed antibodies made according to the method disclosed in Segal et al., U.S. Pat. No. 4,676,980.

Antibodies that bind to the same epitope (i.e., the specific binding site) that is bound by an antibody to the target epitope can be identified in accordance with known techniques, such as their ability to compete with labeled antibody to the target epitope in a competitive binding assay.

Antibody fragments included within the scope of the present invention include, for example, Fab, F(ab')2, and Fc fragments, and the corresponding fragments obtained from antibodies other than IgG. Such fragments can be produced by known techniques.

Monoclonal antibodies may be collected and purified from cultures of immortal cells produced as described above, and prepared for binding assays as described below, in accordance with known techniques.

While antibodies of the present invention are primarily intended for use in screening or as an aid to diagnosis, the antibodies may be also be used for therapeutic treatments such as the treatment of asthma or anaphylactic shock in a human or animal subject (e.g., dog, cat, horse) by administering antibodies to the subject (e.g., by parenteral injection, such as intraveneous injection) in an amount effective to treat the asthma or anaphylactic shock. Such antibodies may be in the forms described above, and in some embodiments may be chimeric antibodies (see, e.g., M. Walker et al., *Molec. Immunol.* 26, 403–11 (1989)) to reduce adverse reactions by the subject thereto.

2. Binding Assays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies as described herein may be directly or indirectly conjugated to a solid support suitable for a diagnostic assay (e.g., beads, plates, slides or wells formed from materials such as latex or polystyrene) in accordance with known techniques, such as precipitation. Antibodies as described herein may likewise be directly or indirectly conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques (e.g., coupling biotin to the antibody, providing a conjugate of avidin and the detectable group, and then binding the conjugate to the antibody by the biotin-avidin binding pair).

As noted above, the present invention particularly provides methods of testing for allergen reactivity of an IgE sample. The methods generally comprise the steps of: (a) contacting a sample containging IgE to a solid support, the solid support having an allergen coupled thereto; and then (b) contacting the solid support to at least one antibody as described above (and in some embodiments to both of the antibodies described above), and then (c) determining the presence or absence of antibody coupled to the solid support, the presence of antibody coupled to the solid support indicating that the IgE in the sample is reactive to the allergen. Where the sample is drawn from a subject, particularly a human or animal subject, the presence of such allergen reactivity is indicative of an allergy to that immunogen in the subject, and/or is an aid to diagnosis of an allergy to that allergen in the subject. The determining step may be carried out by any suitable technique as described above, and in one preferred embodiment is carried out by enzyme-linked immunosorbent assay (ELISA). Any suitable allergen can be coupled to or deposited on the solid support, including but not limited to mold, pollen, dust mite, milk, egg, soy, peanut and corn allergens. The sample may be a biological sample drawn from a subject, particularly a mammalian subject such as a dog, cat or horse (for veterinary purposes) or a human.

In another embodiment, the present invention further provides a method of detecting mammalian IgE, comprising: (a) providing (i) a first antibody as described above that specifically binds to an epitope between amino acid positions 356–374 of a mammalian IgE; and (ii) a second antibody as described above that specifically binds to an epitope between amino acid positions 145–166 of mammalian IgE; (b) contacting a sample suspected of containing mammalian IgE to the first and second monoclonal antibodies, under conditions in which one of the first and second monoclonal antibodies is immobilized on a solid support and the other of the first and second monoclonal antibodies is coupled to a detectable group, so that the detectable group is coupled to the solid support if mammalian IgE is present in the sample; and then (c) detecting the presence or absence of the detectable group on the solid support; the presence of the detectable group on the solid support indicating the presence of mammalian IgE in the sample. Preferably, one of the monoclonal antibodies is coupled to a detectable group (including a member of a specific binding pair, such as avidin, as noted above), and the other of the monoclonal antibodies is coupled to a solid support. Numerous such "sandwich assay" formats are known and can be implemented in accordance with known techniques utilizing the antibodies described herein.

A test kit useful for carrying out the methods of the present invention may comprise: (a) an antibody that specifically binds to an epitope between amino acid positions 356–374 of a mammalian IgE; and (b) an antibody that specifically binds to an epitope between amino acid positions 145–166 of mammalian IgE can be provided in conventional manner. The antibodies can be packaged together in a common package along with instructions for carrying out any of the assays as described above.

The present invention is explained in greater detail in the following non-limiting Examples.

EXAMPLE 1

Screening for Mouse Antibodies Specific for Canine IRE: Hybridoma Production Female BALB/c mice were used as donor mice in the fusion process. The mice were immunized by intraperitoneal injection of 200 µg canine IgE monoclonal antibody (mAb, commercially available from Bethyl Labs, Montgomery, Tex.) in complete Freund's adjuvant (Difco, Detroit, Mich.) twice before final boosting with 150 µg canine IgE in incomplete Freund's adjuvant. Fusions were performed 7 days after this boosting. The fusions were performed using 35% polyethylene glycol (PEG) 1000 (Fisher Scientific, Pittsburgh, Pa.) with $1 \times 10^7$ 0.653 myeloma cells and $1 \times 10^7$ donor spleen cells. The cells were plated at $4 \times 10^4$ cells/well in five 96 well microtiter plates.

EXAMPLE 2

Hybridoma Screening Procedure

Microtiter plates were coated overnight at room temperature with 10 µg/ml canine IgE in 0.05 M carbonate/bicarbonate buffer, pH 9.6. After the plates were washed with phosphate buffered saline (PBS) containing 0.05% TWEEN-20 (PBS-T), the wells were blocked with 1% gelatin in PBS-T for 4 hours. Cell culture supernatants were added to the wells and incubated for 30 minutes at 37° C. The plates were washed again and peroxidase conjugated rabbit antiserum against mouse immunoglobulins (Miles, Naperville, Ill.) was added to the wells. Plates were developed with 2,2' azino-di-(3-ethylbenzthiazoline) sulfonic acid (ABTS, Sigma, St. Louis, Mo.) at 37° C. for 30 minutes in the dark and then read on an ELISA reader at 414 nm. Hybridoma cell culture supernatants were also screened for reactivity with canine IgG by the same procedure using plates coated with 10 µg/ml canine IgG diluted at 1/10. Positive reactors from this screen were discarded.

EXAMPLE 3

Hybridoma Cloning

Hybridomas were cloned by limiting dilution (16) in 96 well microtiter plates with $1 \times 10^4$ feeder cells/well. Feeder cells consisted of peritoneal exudate cells were collected from female BALB/c mice by peritoneal lavage using serum free medium. Cloning was performed at theoretical hybridoma cell concentrations of 100, 10, 1, 0.5 and 0.1 cells/well. The plates were screened visually for hybridomas at 7–10 days after cloning and scored for the number of hybridomas present per well. Wells containing clones were assayed for antibody production and positive clones were cultured before freezing. Positive hybridomas and clones were frozen in a solution of 45% DMEM, 45% fetal calf serum (FCS) and 10% dimethyl sulfoxide (DMSO) and stored in liquid nitrogen. When necessary, frozen cells were thawed at 37° C. and transferred to fresh media. The cells were then centrifuged at 500×g and resuspended in fresh media containing 10% FCS to remove them from DMSO. Thawed hybrids were recloned after they were stable in culture. Two resulting monoclonal antibodies from the recloned hybrids used in the following are 5.91 and 3.76.

EXAMPLE 4

Allergen Screening Procedure: Plate Preparation

Individual wells of a standard 96-well microtiter plates were coated with allergen at 50 µg/ml in 0.01M carbonate/bicarbonate buffer pH 9.0 prepared as described below. The allergen solutions were prepared by dialyzing a specific commercially available allergen (Greer Labs, Lenoir, N.C.) in PBS to remove glycerol vehicle then adding 2-mercaptoethanol at 5% and heating for 5 minutes at 100° C. Precipitates were removed by centrifugation and the resulting supernatant containing denatured allergen was dialyzed against 0.01M carbonate/bicarbonate buffer, pH 9.0. The plates were allowed to set overnight at room temperature, then washed with PBS-T. In order to prevent non-specific binding, the wells were blocked with 0.5% gelatin for 2 hours, and then washed with PBS-T.

EXAMPLE 5

Allergen Screening Procedure: Assay of Test Sera

Fifty microliters of serially diluted test serum in PBS-T, assayed in triplicate, was added to individual wells and incubated for 2–3 hours at room temperature. Following incubation, the wells were washed with PBS-T, incubated for 2 hours with either 1 µg/ml biotinylated 5.91 mAb in PBS-T or 4 µg/ml biotinylated 3.76 mAb in PBS-T for 2 hours at room temperature, and then washed with PBS-T. The plates were then incubated with peroxidase conjugated avidin (KPL Labs, Gaithersburg, Md.) diluted 1/2000 in PBS-T for 30 minutes and developed with ABTS in the dark for 60 minutes-overnight and then read on an ELISA reader at 414 nm.

EXAMPLE 6

Cross-Reactivity of IgE Specific Monoclonal Antibodies

The 5.91 and 3.76 mAbs recognize epitopes on canine IgE corresponding to amino acid residues 356–374 and 145–166 respectively of the canine IgE $\epsilon$-chain. Recognition of $\epsilon$-chains from IgE from cat, horse, pig and human by 5.91 and 3.76 was examined. Both 5.91 and 3.76 were observed to have good cross-reactivity with the $\epsilon$-chain of IgE from cat and horse, but did not exhibit cross-reactivity with either pig or human $\epsilon$-chains of IgE. The amino acid alignment of the regions recognized by 5.91 and 3.76 is shown in Table 1.

TABLE 1

IgE epitopes recognized by mAbs 5.91 and 3.76[a]

5.91 recognition site

| | | |
|---|---|---|
| Dog | RNDSPIQTDQYTTTG | a.a. seq. nos. 357–371 (SEQ ID NO: 1) |
| Cat | HNDSPVRTEQQATTW | a.a. seq. nos. 427–441 (SEQ ID NO: 2) |

TABLE 1-continued

IgE epitopes recognized by mAbs 5.91 and 3.76[a]

| | | |
|---|---|---|
| Horse | RNNVLIQTDQQATTR | a.a. seq. nos. 356–370 (SEQ ID NO: 3) |
| Sheep | RNKELMREGQHTTTQ | a.a. seq. nos. 357–371 (SEQ ID NO: 4) |
| Mouse | GDGKLISNSQHSTTT | a.a. seq. nos. 346–360 (SEQ ID NO: 5) |
| Rat | QDSKLIPKSQHSTTT | a.a. seq. nos. 349–363 (SEQ ID NO: 6) |
| Pig | RNDAPVQADRHSTTR | a.a. seq. nos. 367–381 (SEQ ID NO: 7) |
| Human | HNEVQLPDARHSTTQ | a.a. seq. nos. 360–374 (SEQ ID NO: 8) |

3.76 recognition site

| | | |
|---|---|---|
| Dog | VDGQKATNIFPYTAPGTK | a.a. seq. nos. 146–162 (SEQ ID NO: 9) |
| Cat | VDGQKATNIFPYTAPGKQ | a.a. seq. nos. 216–232 (SEQ ID NO: 10) |
| Horse | IDGQKVDEQFPQHGLVKQ | a.a. seq. nos. 145–161 (SEQ ID NO: 11) |
| Pig | VDGQEDRNLFSYTAPDQL | a.a. seq. nos. 151–168 (SEQ ID NO: 12) |
| Sheep | VDGHESKELYAQPGPEIQ | a.a. seq. nos. 152–169 (SEQ ID NO: 13) |
| Mouse | MDDREITDTLAQTVLIKE | a.a. seq. nos. 137–154 (SEQ ID NO: 14) |
| Rat | MDDRKIYETHAQNVLIKE | a.a. seq. nos. 140–156 (SEQ ID NO: 15) |
| Human | EDGQVMDVDLS-TASTTQ | a.a. seq. nos. 150–166 (SEQ ID NO: 16) |

[a]Pig, Sheep, Mouse and Rat sequences from Vernersson et al. (1997) Immunogenetics 46:461–468.

The foregoing is illustrative of the present invention, and is not to be construed as limiting thereof. The invention is defined by the following claims, with equivalents of the claims to be included therein.

That which is claimed is:

1. An isolated antibody that specifically binds to mammalian IgE at an epitope wherein said epitope is selected from the group consisting of SEQ ID NO:9, SEQ ID NO: 10 and SEQ ID NO:11.

2. The antibody of claim 1, wherein said mammalian IgG is dog IgE and wherein said epitope is a dog IgE epitope SEQ ID NO:9.

3. The antibody of claim 1, wherein said antibody is a monoclonal antibody.

4. The antibody of claim 1, wherein said antibody is a mouse antibody.

5. The antibody of claim 1 coupled to a detectable group.

6. The antibody of claim 1 coupled to a member of a specific binding pair.

7. A method of testing for allergen reactivity of an IgE sample, comprising the steps of:
 (a) contacting a sample containinging IgE to a solid support, said solid support having an allergen coupled thereto; and then
 (b) contacting said solid support to at least one antibody of claim 1, and then
 (c) determining the presence or absence of antibody coupled to said solid support, the presence of antibody coupled to said solid support indicating that said IgE in said sample is reactive to said allergen.

8. The method of claim 7, wherein said determining step is carried out by enzyme-linked immunosorbent assay (ELISA).

9. The method of claim 7, wherein said allergen is selected from the group consisting of mold, pollen, dust mite, milk, egg, soy, peanut and corn allergens.

10. The method of claim 7, wherein said sample is a biological sample collected from a dog, cat or horse.

11. A test kit, comprising:
 (a) a monoclonal antibody that specifically binds to an epitope of a mammalian IgE wherein said epitope is selected from the group consisting of SEQ ID NO:1, SEQ ID NO:2, and SEQ ID NO:3; and
 (b) a monoclonal antibody that specifically binds to an epitope of mammalian IgE wherein said epitope is selected from the group consisting of SEQ ID NO:9, SEQ ID NO:10, and SEQ ID NO:11.

12. The test kit of claim 11, wherein at least one of said monoclonal antibodies is coupled to a detectable group.

\* \* \* \* \*

UNITED STATES PATENT AND TRADEMARK OFFICE
CERTIFICATE OF CORRECTION

PATENT NO. : 7,148,023 B2
APPLICATION NO. : 10/758165
DATED : December 12, 2006
INVENTOR(S) : Hammerberg It is certified that error appears in the above-identified patent and that said Letters Patent is hereby corrected as shown below:

Column 1,
Line 43 should read -- antibodies bind is dog IgE. --

Column 13,
Line 16 should read -- 2. The antibody of claim 1, wherein said mammalian IgE --

Signed and Sealed this

Tenth Day of April, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 15
<212> TYPE: PRT
<213> ORGANISM: Canis familiaris

<400> SEQUENCE: 1

Arg Asn Asp Ser Pro Ile Gln Thr Asp Gln Tyr Thr Thr Thr Gly
1               5                   10                  15

<210> SEQ ID NO 2
<211> LENGTH: 15
<212> TYPE: PRT
<213> ORGANISM: Felis catus

<400> SEQUENCE: 2

His Asn Asp Ser Pro Val Arg Thr Glu Gln Gln Ala Thr Thr Trp
1               5                   10                  15

<210> SEQ ID NO 3
<211> LENGTH: 15
<212> TYPE: PRT
<213> ORGANISM: Equus caballus

<400> SEQUENCE: 3

Arg Asn Asn Val Leu Ile Gln Thr Asp Gln Gln Ala Thr Thr Arg
1               5                   10                  15

```
<210> SEQ ID NO 4
<211> LENGTH: 15
<212> TYPE: PRT
<213> ORGANISM: Ovis aries

<400> SEQUENCE: 4

Arg Asn Lys Glu Leu Met Arg Glu Gly Gln His Thr Thr Thr Gln
1               5                   10                  15

<210> SEQ ID NO 5
<211> LENGTH: 15
<212> TYPE: PRT
<213> ORGANISM: Mus musculus

<400> SEQUENCE: 5

Gly Asp Gly Lys Leu Ile Ser Asn Ser Gln His Ser Thr Thr Thr
1               5                   10                  15

<210> SEQ ID NO 6
<211> LENGTH: 15
<212> TYPE: PRT
<213> ORGANISM: Rattus norvegicus

<400> SEQUENCE: 6

Gln Asp Ser Lys Leu Ile Pro Lys Ser Gln His Ser Thr Thr Thr
1               5                   10                  15

<210> SEQ ID NO 7
<211> LENGTH: 15
<212> TYPE: PRT
<213> ORGANISM: Sus scrofa

<400> SEQUENCE: 7

Arg Asn Asp Ala Pro Val Gln Ala Asp Arg His Ser Thr Thr Arg
1               5                   10                  15

<210> SEQ ID NO 8
<211> LENGTH: 15
<212> TYPE: PRT
<213> ORGANISM: Homo sapiens

<400> SEQUENCE: 8

His Asn Glu Val Gln Leu Pro Asp Ala Arg His Ser Thr Thr Gln
1               5                   10                  15

<210> SEQ ID NO 9
<211> LENGTH: 18
<212> TYPE: PRT
<213> ORGANISM: Canis familiaris

<400> SEQUENCE: 9

Val Asp Gly Gln Lys Ala Thr Asn Ile Phe Pro Tyr Thr Ala Pro Gly
1               5                   10                  15

Thr Lys

<210> SEQ ID NO 10
<211> LENGTH: 18
<212> TYPE: PRT
<213> ORGANISM: Felis catus

<400> SEQUENCE: 10

Val Asp Gly Gln Lys Ala Thr Asn Ile Phe Pro Tyr Thr Ala Pro Gly
1               5                   10                  15
```

Lys Gln

```
<210> SEQ ID NO 11
<211> LENGTH: 18
<212> TYPE: PRT
<213> ORGANISM: Equus caballus

<400> SEQUENCE: 11
```

Ile Asp Gly Gln Lys Val Asp Glu Gln Phe Pro Gln His Gly Leu Val
1               5                   10                  15

Lys Gln

```
<210> SEQ ID NO 12
<211> LENGTH: 18
<212> TYPE: PRT
<213> ORGANISM: Sus scrofa

<400> SEQUENCE: 12
```

Val Asp Gly Gln Glu Asp Arg Asn Leu Phe Ser Tyr Thr Ala Pro Asp
1               5                   10                  15

Gln Leu

```
<210> SEQ ID NO 13
<211> LENGTH: 18
<212> TYPE: PRT
<213> ORGANISM: Ovis aries

<400> SEQUENCE: 13
```

Val Asp Gly His Glu Ser Lys Glu Leu Tyr Ala Gln Pro Gly Pro Glu
1               5                   10                  15

Ile Gln

```
<210> SEQ ID NO 14
<211> LENGTH: 18
<212> TYPE: PRT
<213> ORGANISM: Mus musculus

<400> SEQUENCE: 14
```

Met Asp Asp Arg Glu Ile Thr Asp Thr Leu Ala Gln Thr Val Leu Ile
1               5                   10                  15

Lys Glu

```
<210> SEQ ID NO 15
<211> LENGTH: 18
<212> TYPE: PRT
<213> ORGANISM: Rattus norvegicus

<400> SEQUENCE: 15
```

Met Asp Asp Arg Lys Ile Tyr Glu Thr His Ala Gln Asn Val Leu Ile
1               5                   10                  15

Lys Glu

```
<210> SEQ ID NO 16
<211> LENGTH: 17
<212> TYPE: PRT
<213> ORGANISM: Homo sapiens
```

-continued

```
<400> SEQUENCE: 16

Glu Asp Gly Gln Val Met Asp Val Asp Leu Ser Thr Ala Ser Thr Thr
1               5                   10                  15

Gln
```